(12) United States Patent
Silber

(10) Patent No.: US 7,389,135 B2
(45) Date of Patent: Jun. 17, 2008

(54) DUAL ELECTRODE WITH THREE STUDS FOR IMPEDANCE CARDIOGRAPHY

(75) Inventor: Daniel A. Silber, Lexington, MA (US)

(73) Assignee: Koninklijke Philips Electronics, N.V., Eindhoven (NL)

( * ) Notice: Subject to any disclaimer, the term of this patent is extended or adjusted under 35 U.S.C. 154(b) by 238 days.

(21) Appl. No.: 10/550,211

(22) PCT Filed: Mar. 4, 2004

(86) PCT No.: PCT/IB2004/000901

§ 371 (c)(1),
(2), (4) Date: Sep. 21, 2005

(87) PCT Pub. No.: WO2004/084985

PCT Pub. Date: Oct. 7, 2004

(65) Prior Publication Data

US 2007/0118031 A1    May 24, 2007

Related U.S. Application Data

(60) Provisional application No. 60/458,796, filed on Mar. 28, 2003.

(51) Int. Cl.
*A61B 5/04* (2006.01)
(52) U.S. Cl. .................. 600/393; 600/391
(58) Field of Classification Search .......... 600/391–393
See application file for complete search history.

(56) References Cited

U.S. PATENT DOCUMENTS 6,415,170 B1  7/2002  Loutis et al.
6,636,754 B1 * 10/2003  Baura et al. .................. 600/393

FOREIGN PATENT DOCUMENTS

| EP | 0 142 372 A | 5/1985 |
|----|-------------|--------|
| GB | 2 070 438 A | 9/1981 |

* cited by examiner

*Primary Examiner*—Lee S Cohen
(74) *Attorney, Agent, or Firm*—Tony Piotrowski

(57) ABSTRACT

A quick-connecting dual electrode assembly for use in procedures such as impedance cardiography includes a body having a cable side and a patient side, and three eyelets arranged therein. A distal snap assembly having a distal stud (108) is secured in a first eyelet (101a) of said three eyelets (101a, 102a, 105a) near an end of the body. An additional stud (105) is arranged in a second eyelet (105a) near a center of the body, wherein the distal stud (108) and the additional stud (105) are electrically joined by a jumper assembly. A proximal snap assembly having a proximal stud (106) secured in a third eyelet (102a) at an opposite end from where the distal stud (108) is arranged proximally to the additional stud (105), so that a distance between the proximal stud (106) and the additional stud (105) is substantially less than a distance between the distal stud (180) and the additional stud (105). The additional stud (105) is electrically isolated from the patient side, and a gel portion is arranged on the patient side of the body for the first stud and the third stud. The electrode apparatus facilitates quick connection of a small dual plug so that the dual plug does not have to be the length of the distance between the two electrically connected studs, yet keeps the electrodes in contact with the patient at an optimum distance apart.

21 Claims, 3 Drawing Sheets

CROSS-SECTION

PATIENT SIDE

CROSS-SECTION

CABLE SIDE

DUAL ELECTRODE WITH THREE STUDS FOR IMPEDANCE CARDIOGRAPHY

CROSS REFERENCE TO RELATED APPLICATION

This application claims the benefit of U.S. provisional application Ser. No. 60/458,796 filed Mar. 28, 2003, which is incorporated herein by reference.

BACKGROUND OF THE INVENTION

1. Field of Invention

The present invention relates to medical electrodes. More particularly, the present invention relates to medical electrodes that can be used in impedance cardiography.

2. Description of the Related Art

Impedance cardiography (ICG) is a medical test to determine the pumping capacity of the heart. ICG is a non-invasive and cost-efficient technique for determining stroke volume (SV), cardiac output (CO), and thoracic fluid volume (TFC, or ZO). Impedance cardiography is also referred to as "Non-Invasive Continuous Cardiac Output" (NiCCO). Impedance cardiography also provides the physician with a measurement of cardiac output without the need for catheterization, an invasive procedure that is expensive and poses some risk to the patient.

ICG normally requires four pairs of electrodes, each pair spaced approximately 50 mm apart. Existing products in the prior art require separate cable connections for each of the electrodes.

To date, there is one double electrode being used 5 for impedance cardiography by CardioDynamics of San Diego, Calif. This product has two sensing elements, separated by 50 mm, each electrode connected directly to the same size snap stud. The prior art also includes single-electrode sensors which have offset studs. In some cases, the offset was done to minimize migration of corrosive coupling agents. In other cases, a single electrode was provided to make two connection points.

However, there is a need in the art for an electrode structure that permits electrodes to be connected quickly without separate cables.

SUMMARY OF THE INVENTION

The present invention provides a disposable medical electrode pair with an additional stud that is mounted near one stud but is electrically connected to the other, thus bringing the two connection points close together and allowing the pair of electrodes to be connected simultaneously with a two-conductor connector. In other words, instead of requiring a dual connector to be larger than the (50 mm) distance between the two electrodes, the current dual electrode assembly permits use of a much smaller connector that is only slightly larger than the distance between the proximal stud and the additional stud, yet keeps the electrodes on the patient side spaced at the optimal distance.

According to an aspect of the invention, the arrangement of the two connections close together advantageously allows the simultaneous connection of both, which permits increased speed of installation and convenience to the practitioner. Such increased speed and convenience can be critical, especially since this invention could be used on patients requiring emergency life-saving care. Accordingly, the increased speed and convenience is extremely desirable.

In addition, the arrangement of the two connections close together allows securing the two wires to each other, reducing the tendency of the capacitance between the wires to change and create electrical noise.

Moreover, the arrangement of the two connections together makes the system less intrusive for the patient, so it appears to the patient that four connections are being made instead of eight.

According to an aspect of the invention, the medical electrode or sensor preferably would be disposable. Making the double electrode more convenient to use also discourages users from substituting individual standard ECG electrodes, a practice that would introduce variability into the test results.

BRIEF DESCRIPTION OF THE DRAWINGS

FIG. 1b illustrates a cross-section view of the electrode apparatus shown in FIG. 1a.

DETAILED DESCRIPTION OF THE INVENTION

It is understood by persons of ordinary skill in the art that the illustrations and description herein are provided for purposes of explanation, and the claimed invention is not limited to the embodiments shown and described, as an artisan can make variations in the design that lie within the spirit of the invention and the scope of the appended claims.

Figure 1A:
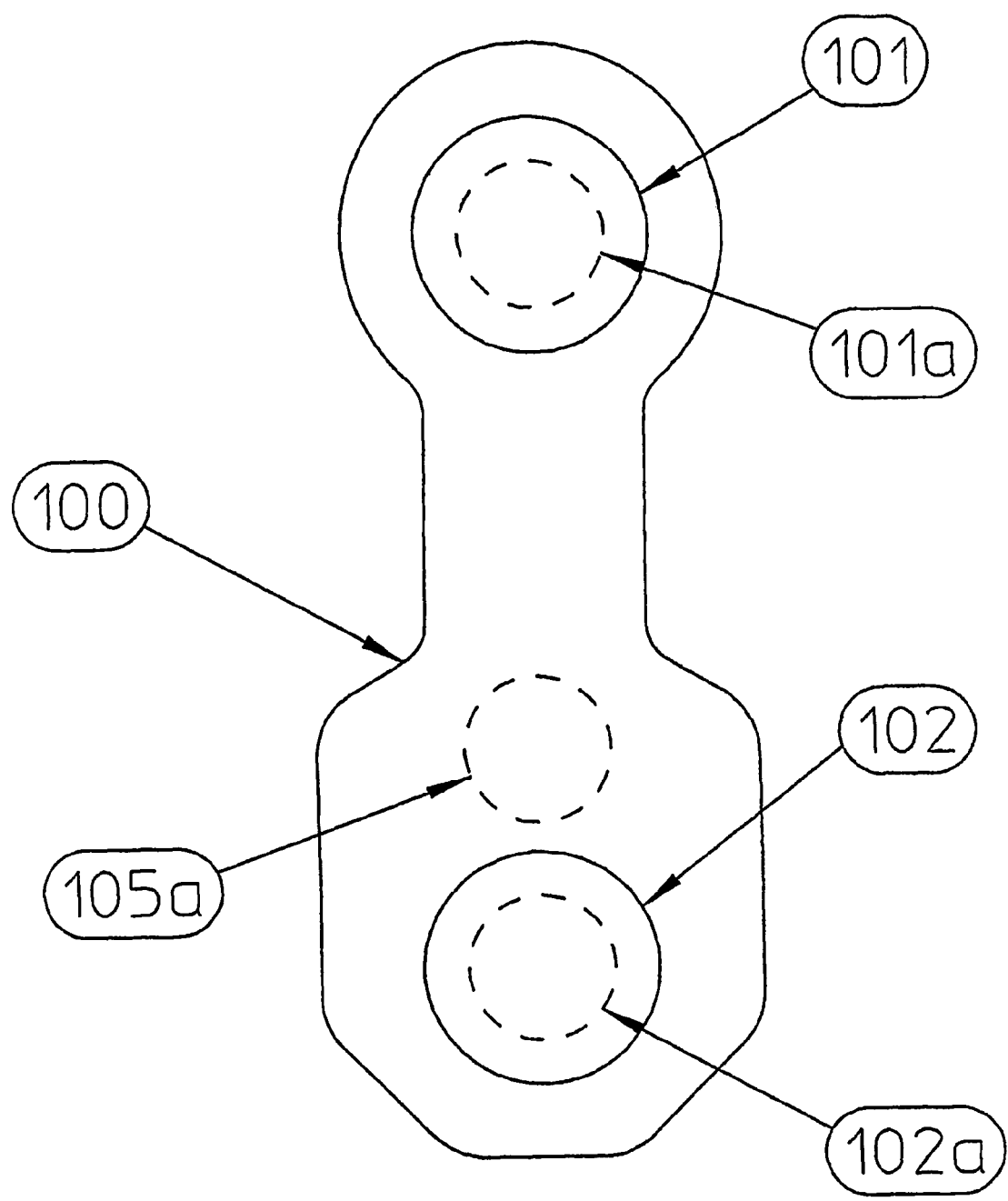
FIG. 1a illustrates a patient-side perspective of an aspect of the electrode apparatus according to the present invention.
Figure 1B:
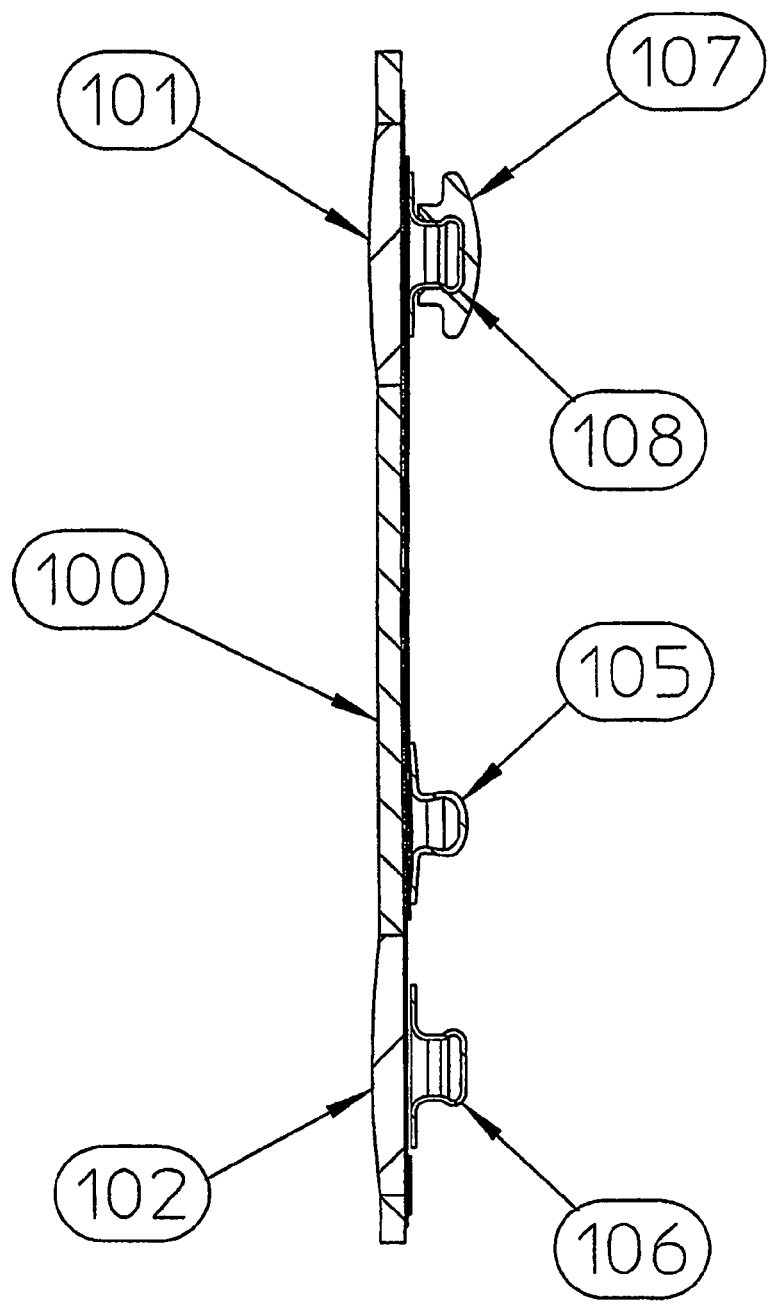

FIG. 1a shows the patient side of an electrode apparatus according to the present invention. The body of electrode 100, in a best mode, would comprise a pressure sensitive adhesive-coated foam similar to that used in other electrodes. However, a solid gel 101, 102 (shown in FIG. 1a) is preferred over a liquid gel. A liquid gel would be poured into the cavities in the assembly after the studs, label, etc. are assembled to the foam. The gel sections 101, 102, each of which may be a differing size and shape, adhere to the eyelets (base) 101a, 102a, each part of a snap assembly, which are secured to the foam base when the stud parts 106, 108 of the assembly are pressed on.

Adhesive on the label 103 secures it to the foam 100, as holes in the foam form wells for the gels. The distal snap assembly 101a, 108 includes an eyelet 101a and a distal stud 108, and the distal snap assembly also secures one end of an electrically-conductive jumper 104 and may be covered by an electrically insulating cap 107 of various designs. The electrically-conductive jumper may be made from foil, plated plastic, or other material or even printed on the label, and may include an insulating layer if required.

Figure 1C:
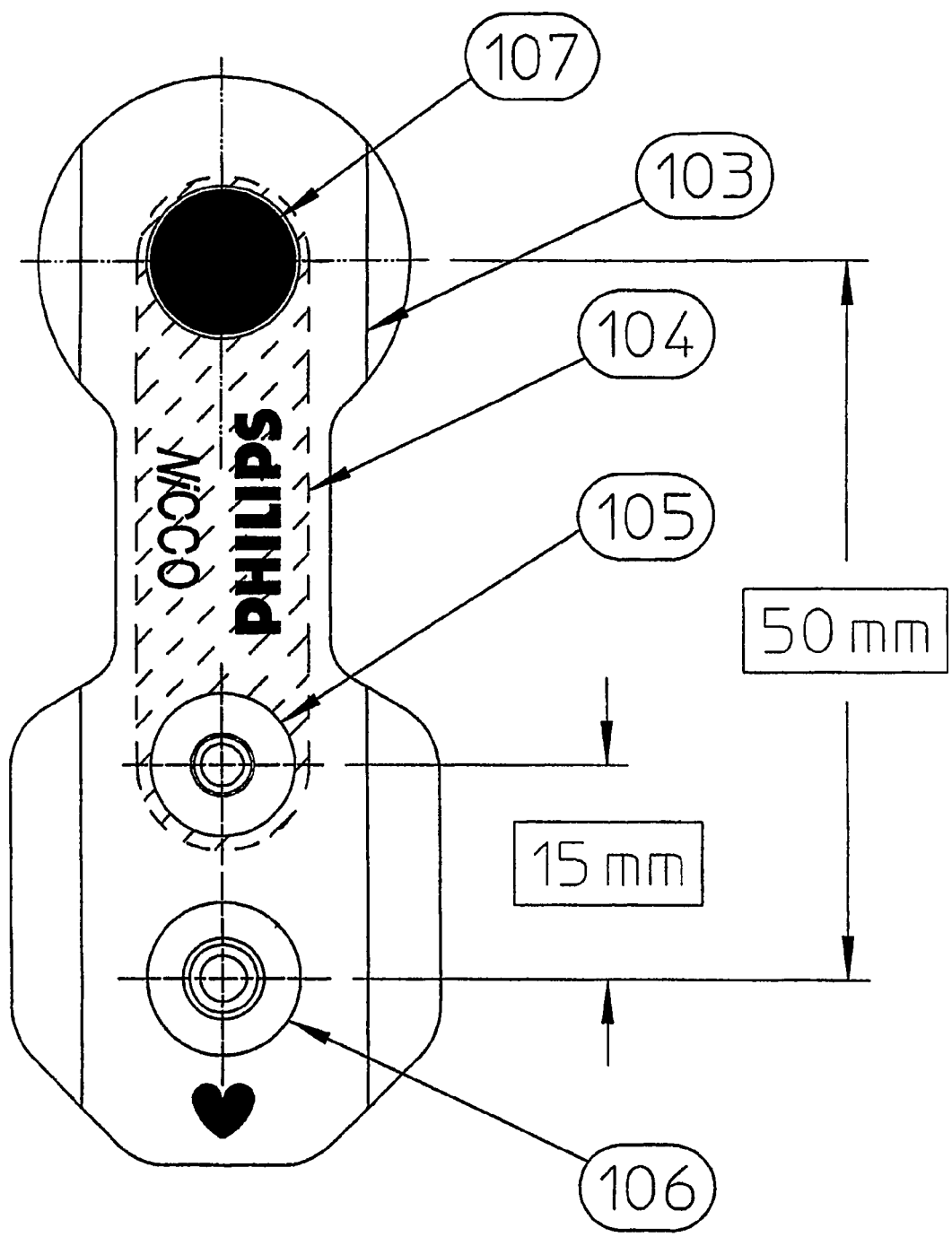
FIG. 1c illustrates a cable-side perspective of an aspect of the electrode apparatus according to the present invention.

The additional snap assembly 105a, 105 includes eyelet 105a and additional stud 105, and this assembly secures the proximal end of the jumper, but it is electrically isolated from the patient. This is achieved by securing it to the label, without penetrating the foam, or by using a non-conductive eyelet 105a (FIG. 1a) or by other means. The final result is two solid gel sections 101, 102 on the patient side (shown in FIG. 1a) arranged substantially 50 mm apart, and an additional stud 105 located substantially 15 mm from proximal stud 106 and 35 mm from distal stud 108 (FIG. 1c).

The connections are preferably made to the additional stud 105 and to the proximal stud 106, approximately 15 mm from it. Ideally, the additional stud 105 can be a different size than the proximal and distal studs 106, 108 that hold the electrode gels, thus precluding inadvertent exchange of the two connections. Ideally, the connector on the cable side can conveniently make both connections simultaneously.

Some of the many aspects of the instant invention, in addition to those previously mentioned in the summary of the invention, include that the electrode is compatible with a very inexpensive cable if it is necessary to forego a double connector type cable for a lower-cost cable with separate connectors, in which case, the stud cover 107 is removed, preferably without the need for tools, and discarded. Then connections are made to the distal stud 108 and the proximal stud 106 using commonly available snap fittings or grabber fittings, which are generally used on ECG cables.

Various modifications can be made to the instant invention by persons of ordinary skill in the art that would not depart from the spirit of the invention or the scope of the appended claims. For example, the distances between the studs, although currently proposed so as to be compatible with certain medical standards, could be varied. The shape and/or size of the studs, etc. can be different from those previously shown. The relative sizes of the studs can also be different. Other types of fittings could be substituted, and such fittings also would not depart from the spirit of the invention and the scope of the appended claims.

What is claimed is:

1. A quick connecting dual electrode assembly comprising:
   a body having a cable side and a patient side, and three eyelets arranged in said body;
   a distal snap assembly comprising a distal stud securing a first eyelet of said three eyelets near an end of the body, and an additional stud securing a second eyelet arranged near a center of the body, wherein said distal stud and said additional stud are electrically joined by a jumper assembly;
   a proximal snap assembly comprising a proximal stud securing a third eyelet at an opposite end from where said distal stud is arranged and proximal to the additional stud, so that a distance between said proximal stud and said additional stud is substantially less than a distance between said distal stud and said proximal stud;
   wherein said additional stud is electrically isolated from said patient side at the location of the additional stud.

2. The electrode assembly according to claim 1, wherein said second eyelet is non-conductive.

3. The electrode assembly according to claim 1, wherein the patient side of the body is coated with an adhesive.

4. The electrode assembly according to claim 1, wherein the patient side of the body includes a first solid gel portion that adheres to the first eyelet and a second solid gel portion that adheres to the third eyelet.

5. The electrode assembly according to claim 1, wherein the patient side of the body includes a first liquid gel portion that adheres to the first eyelet and a second liquid gel portion that adheres to the third eyelet, and the first liquid gel portion and the second liquid gel portion are about 50 mm apart.

6. The electrode assembly according to claim 1, wherein the jumper assembly comprises foil.

7. The electrode assembly according to claim 6, wherein the jumper assembly has a label printed thereon.

8. The electrode assembly according to claim 1, wherein the jumper assembly comprises plated plastic.

9. The electrode assembly according to claim 1, wherein the distance between said distal stud and said additional stud is about 35 mm apart.

10. The electrode assembly according to claim 9, wherein the distance between said distal stud and said proximal stud is about 50 mm.

11. The electrode assembly according to claim 9, wherein the distance between the additional stud and the proximal stud is about 15 mm.

12. The electrode assembly according to claim 1, wherein electrical connections are made on the cable side of the body to the additional stud and the proximal stud.

13. The electrode assembly according to claim 12, wherein the additional stud is a different size than the proximal stud and the distal stud.

14. The electrode assembly according to claim 1, wherein the distal stud has a removable cover.

15. The electrode assembly according to claim 14, wherein the cover is electrically insulating.

16. The electrode assembly according to claim 1, wherein the additional stud and proximal stud are sized to receive a two-stud connector plug thereon.

17. A method of making a dual-electrode assembly comprising the steps of:
   (a) providing a body having a cable side and a patient side, and three eyelets arranged in said body;
   (b) providing a distal snap assembly comprising a distal stud securing a first eyelet of said three eyelets near an end of the body, and an additional stud securing a second eyelet arranged near a center of the body, wherein said distal stud and said additional stud are electrically joined by a jumper assembly;
   (c) providing a proximal snap assembly comprising a proximal stud securing a third eyelet at an opposite end from where said distal stud is arranged and proximal to the additional stud, so that a distance between said proximal stud and said additional stud is substantially less than a distance between said distal stud and said additional stud; and
   (d) isolating said additional stud from said patient side at the location of the additional stud.

18. The method according to claim 17, further comprising:
   (e) arranging a first solid gel portion on the patient side of the first eyelet; and
   (f) arranging a second solid gel portion on the patient side of the third eyelet, so that said first gel portion and said second gel portion are about 50 mm apart.

19. The method according to claim 17, further comprising:
   (e) sizing the additional stud at a different diameter than the distal stud and the proximal stud.

20. The method according to claim 19, wherein the diameter of the additional stud is larger than at least one of the proximal stud and the distal stud.

21. The method according to claim 17, further comprising (e) shaping the additional stud in a different shape than at least one of the proximal stud and distal stud.

* * * * *